United States Patent
Gaffin et al.

(10) Patent No.: US 6,670,170 B1
(45) Date of Patent: Dec. 30, 2003

(54) TEMPERATURE-REGULATED CELL PERIFUSION CHAMBER

(75) Inventors: Stephen L. Gaffin, Framingham, MA (US); Michael Koratich, Springville, AL (US); David E. Lewis, Grafton, MA (US); Bruce Smith, Grafton, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/571,406

(22) Filed: May 15, 2000

(51) Int. Cl.$^7$ ................................. C12M 1/34
(52) U.S. Cl. ................... 435/288.4; 435/288.3; 435/305.3
(58) Field of Search .................. 435/291, 283, 435/297.1, 287.2, 284.1, 288.3, 288.4, 305.3

(56) References Cited

U.S. PATENT DOCUMENTS

| | | | |
|---|---|---|---|
| 3,726,597 A | | 4/1973 | Dvorak et al. |
| 4,242,459 A | * | 12/1980 | Chick et al. ............... 435/283 |
| 4,395,492 A | | 7/1983 | Rees |
| 4,734,372 A | | 3/1988 | Rotman |
| 4,764,952 A | | 8/1988 | Feliu |
| 5,241,415 A | | 8/1993 | Argentieri et al. |
| 5,512,480 A | | 4/1996 | Sandstrom et al. |
| 5,527,705 A | * | 6/1996 | Mussi et al. ............. 435/297.1 |
| 5,567,617 A | | 10/1996 | Caprio et al. |

OTHER PUBLICATIONS

Poyton et al.; "A Multipurpose Microperfusion Chamber"; *Experimental Cell Research*; 1970; pp. 109–114; vol. 60; Berkley, California (No month).

Forsythe; "Microincubator for Regulating Temperature and Superfusion of Tissue–Cultured Neurons during Electrophysiological or Optical Studies"; *Methods in Neurosciences*; 1991; pp. 301–318; vol. 4; Academic Press (No month).

* cited by examiner

*Primary Examiner*—Deborah Jones
*Assistant Examiner*—Jane Rhee
(74) *Attorney, Agent, or Firm*—Elizabeth Arwine

(57) ABSTRACT

A cell perifusion chamber structure capable of continuously monitoring processes during polymerase chain reaction includes a cell chamber body having a support surface with an aperture defined through the support surface, and wall structure extending upwardly from the support surface to define an interior. The wall structure includes passages therein. A gasket is disposed on the support surface so as not to cover the aperture. A first transparent cover is disposed on the gasket so as to cover the aperture. A water bath body is provided and has a first portion and a second portion extending from the first portion. The first portion defines a second support surface. The second portion is received in the interior of the cell chamber body and is in interference fit arrangement with the wall structure. The water bath body has an interior support surface with an aperture therethrough. The aperture extends through the first and second portions. The first portion has first ports therein which communicate with the aperture of the water bath body. The second portion includes second ports therein which communicate with the aperture of the water bath body and with associated passages in the cell chamber body. A second transparent cover is disposed on the interior support surface of the water bath body so as to divide the aperture of the water bath body into first and second portions. The second transparent cover covers the second portion of the aperture to define a sealed cell chamber enclosed by the second transparent cover, the first transparent cover and surfaces of the cell chamber body. A transparent window is disposed on the second support surface to cover the first portion of the aperture to define a water bath chamber enclosed by the transparent window, the second cover and surfaces of the water bath body. Whereby fluid may enter and exit the water bath chamber via first ports and perifusion fluid may enter and exit the cell chamber via the second ports.

10 Claims, 1 Drawing Sheet

TEMPERATURE-REGULATED CELL PERIFUSION CHAMBER

FIELD OF THE INVENTION

The invention relates to a temperature-regulated cell perifusion chamber for use in microscopy, cell imaging, cell culture and cell biology.

BACKGROUND OF THE INVENTION

The development of new techniques in cell culture has successfully led to the growing of pure lines of many types of mammalian cells. However, exploitation of the availability of new pure cell cultures is impeded by the lack of appropriate instrumentation. Specifically, it is currently difficult or impossible by commercial instruments to continuously observe mammalian cells under an optical microscope at high power, while at the same, time, controlling temperature and altering it as appropriate, and maintaining the composition and sterility of a defined growth medium or altering it as appropriate.

One method of studying the intracellular composition of cells is by means of fluorescence imaging. In this system, a narrow laser beam is directed through a microscope onto cells attached to a glass surface. Fluorescence within the cells induced by the laser is digitally recorded, amplified by a photomultiplier fixed to the microscope, and analyzed by computer. By loading cells with specialized commercially available fluorescence dyes one can study changes in concentrations of intracellular sodium, potassium, calcium, and hydrogen ions, as well as membrane voltage and membrane fluidity, and almost any other material to which a specific antibody can be produced and labeled with a fluorescence dye. For this method to be successful, the cells must be firmly attached to a transparent surface and remain immobile during the entire experimental procedure. Furthermore, the temperature of the medium bathing the cells must be absolutely controlled.

An important type of experiment is to determine the effects of various pharmacological agents, electrolytes, nutrients and environment on the composition, interactions and structure of cells and subcellular compartments. In order to carry out such studies, it is necessary to fix the cell to a transparent glass or Pyrex surface, take fluorescent measurements and change the composition of the medium bathing the cells with a new solution containing the compound under study while constantly or periodically recording the fluorescence. While a few cell types adhere tightly to a glass surface and are conveniently studied, many cell types, among the most interesting and important, do not adhere strongly to glass. In a conventional cell chamber used in such studies, the physical process of removing the old solution (aspiration) and exchanging it with a new one (pipetting) detaches the cells, causing them to move and often to float away so that the fluorescence measurements are useless. Furthermore, it is difficult to maintain rigid temperature control in such chambers.

Conventional cell perifusion chambers have one or more of the following disadvantages: are manufactured of metals which may partially deteriorate under acidic or alkaline conditions leading to toxic activity toward cells, may alter optical path by assembly by the uneven tightening of screws, may be difficult to clean, have slow rates of temperature change and are of heavy mass, composed of many parts which must be cleaned and assembled each time, may not have the capacity for thermoregulation, or the cell chamber is unenclosed and open to the atmosphere and not providing protection against pathogens.

Thus, there is a need for a Cell Perifusion Chamber:
1. that is of durable construction so that it may be used with little regard to mechanical failure under harsh conditions,
2. That is constructed of biocompatible material to permit normal cell growth,
3. that is of low mass to prevent distortions in the optical path on a microscope and can be used in space science in a low cost in mass,
4. that can withstand heat, acid and alkali so that it can be sterilized by several methods,
5. that can be temperature-controlled within ranges appropriate for living cells,
6. in which the temperature can be changed rapidly,
7. that can permit exchange of solutions (perifusion) which is so gentle that the cell is not disturbed and remains unmoved on its glass surface,
8. that can be used with a standard 35mm microscope stage insert,
9. that can be completely sealed to safely observe pathogens and other hazardous materials for prolonged periods of time,
10. that is of simple design permitting easy and rapid assembly and disassembly for cleaning and sterilization,
11. in which the optical path through the cell is uniform and not distorted significantly by variations in sealing pressure during assembly.

SUMMARY OF THE INVENTION

An object of the present invention is to fulfill the need referred to above. In accordance with the principles of the preset invention, this objective is obtained by providing a temperature-regulated cell perifusion chamber that permits the observation of cells under a microscope at high power (e.g., 1000 x), over a prolonged period of time (hours to weeks), is suitable for fluorescence imaging experiments, while permitting the simultaneous changing of the medium bathing the cells, maintaining the sterility of the medium and absolutely controlling temperature.

The cell perifusion chamber structure includes a cell chamber body having a support surface with an aperture defined through the support surface, and wall structure extending upwardly from the support surface to define an interior. The wall structure includes passages therein. A gasket is disposed on the support surface so as not to cover the aperture. A first transparent cover is disposed on the gasket so as to cover the aperture. A water bath body is provided and has a first portion and a second portion extending from the first portion. The first portion defines a second support surface. The second portion is received in the interior of the cell chamber body and is in interference fit arrangement with the wall structure. The water bath body has an interior support surface with an aperture therethrough. The aperture extends through the first and second portions. The first portion has first ports therein which communicate with the aperture of the water bath body. The second portion includes second ports therein which communicate with the aperture of the water bath body and with associated passages in the cell chamber body. A second transparent cover is disposed as on the interior support surface of the water bath body so as to divide the aperture of the water bath body into first and second portions. The second transparent cover covers the second portion of the aperture to define a sealed cell chamber enclosed by the second transparent cover, the first transparent cover and surfaces of the cell chamber body. A transparent window is disposed on the second support surface to cover the first portion of the aperture to define a water bath chamber enclosed by the transparent window, the second cover and surfaces of the water bath body. Fluid may enter and exit the water bath chamber via first ports to regulate temperature of the cell chamber via heat exchange therewith, and perifusion fluid may enter and exit the cell chamber via the second ports.

In accordance with another aspect of the invention, a method of regulating temperature of a cell perifusion chamber includes:

providing a sealed cell chamber and a transparent cover in the cell chamber, the transparent cover supporting cells to be studied, providing a water bath chamber defined by surfaces which are in heat exchange relation with surfaces defining the cell chamber, the water, bath chamber being fluidly isolated from the cell chamber, supplying temperature regulating fluid flow through the cell chamber so as to regulate a temperature of the cell chamber, and supplying perifusion fluid flow to through the cell chamber.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF PREFERRED EMBODIMENTS

Figure 1:
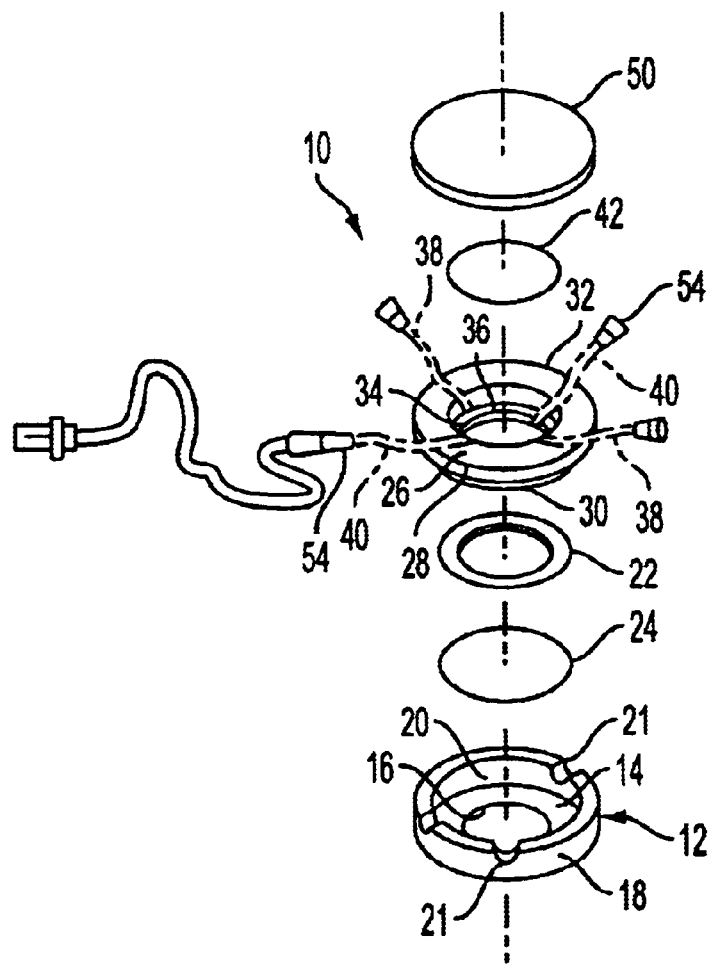
FIG. 1 is an exploded view of a cell perifusion chamber structure provided in accordance with the principles of the present invention.
Figure 2:
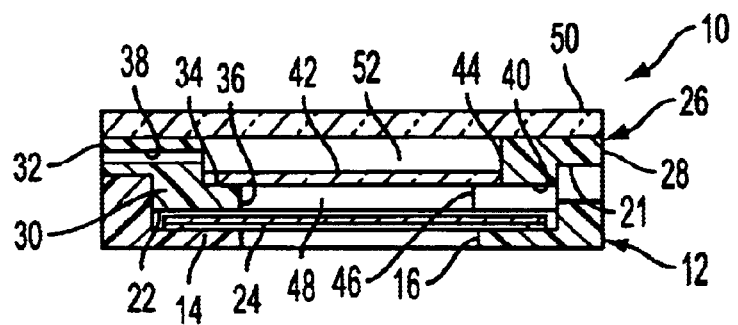
FIG. 2 is a cross-sectional view of the perifusion chamber structure of FIG. 1 in an assembled condition.

With reference to FIGS. 1 and 2, a cell perifusion chamber structure provided in accordance with the principles of the present invention is shown generally indicated at 10. The structure 10 includes a cell chamber body, generally indicated at 12, having a support surface 14 with an aperture 16 defined through the support surface 14. A wall structure 18 extends upwardly from the support surface 14 to define a cylindrical interior 20. The wall structure 18 including passages 21 therein, the function of which will be explained below.

A gasket 22 is disposed on the support surface 14 so as not to cover the aperture 16. In the embodiment, the gasket 22 is an elastomeric material such as silicone or other non-toxic material that can withstand being autoclaved or being exposed to one normal hydrochloric acid or normal NaOH. The gasket 22 is preferably bonded to the support surface 14 by silicone cement or adhesive. An optically transparent cover 24 is disposed on the gasket 22 so as to cover the aperture 16.

A water bath body, generally indicated at 26, has a first diameter portion 28 and a second diameter portion 30 extending therefrom. The first and second portions 28 and 30, respectively, are thus cylindrical. The first diameter portion defines a second support surface 32. The second diameter portion 30 is smaller than the first diameter portion 28 and the second diameter portion 30 is received in the interior 20 of the cell chamber body 12 and is in interference fit arrangement with the wall structure 18. The water bath body 26 has an interior support surface 34 with an aperture 36 therethrough. The aperture 36 extends through the first and second diameter portions 28 and 30, respectively. The first diameter portion 28 has a pair of first ports 38 therein which communicate with the aperture 36 of the water bath body 26. The second diameter portion 30 includes a pair of second ports 40 therein which communicate with the aperture 36 and with associated passages 21 in the cell chamber body 12.

A second transparent cover 42 is disposed on the interior support surface 34 of the water bath body 26 so as to divide the aperture 36 into a first portion 44 and a second portion 46 (FIG. 2). The second transparent cover 42 covers the second portion 46 of the aperture 36 to define a cell perifusion chamber 48 enclosed by the second transparent cover 42, the first transparent cover 24 and surfaces of the cell chamber body 12.

A transparent window 50 is disposed on the second support surface 32 to cover the first portion 44 of the aperture 36 to define a water bath chamber 52 enclosed by the transparent window 50, the second cover 42 and surfaces of the water bath body 26.

In order to permit heat and chemical sterilization, the cell chamber body 12 and water bath body 26 should be constructed of tough plastic materials which are biocompatible, and tolerant of a temperature of 120° C. and to hydrochloric acid and sodium hydroxide solutions at concentrations of 1 Normal for three hours without significant deformation.

If the cell perifusion chamber 48 is to be used to measure fluorescence in the ultraviolet region of the spectrum, then the first transparent cover 24 should either be composed of quartz or be thinner than normal coverslips. However, this is an unusual condition and for many purposes the covers 24 and 42 can be constructed of Pyrex, glass or non-fluorescent clear plastic.

As shown in FIG. 1, a syringe needle is associated with each of the ports 38 and 40 for supplying and removing fluid from the chambers 48 and 52. Temperature-regulated fluid enters and leaves the water bath chamber 52 via ports 38 through two syringe,needles 54. This is normally a continuous process, but may be discontinuous. Perifusion fluid in cell chamber 48 enters and leaves ports 40 and 21 through the other two syringe needles 54. This normally is an intermittent process, but may be continuous.

The dimensions of the chambers 48 and 52 are constrained by: a) the physical requirements of fitting into a 35 mm diameter chamber holder of a microscope stage, and b) an obstructed area on the cell attachment base enabling a 100× oil immersion objective or other objectives to focus onto the internal glass surface of cover 24.

Because of the optical requirements of most standard 100× microscope objectives, cover 24 to which cells adhere, should be as thin as possible, which can be met by using a commercial thin-walled (#1 gauge) glass microscope coverslip, or equivalent. If less powerful objectives or special optics are employed, then thicker and stronger glass microscope coverslips may be used.

The window 50 of the water bath chamber 52 should be transparent in order to observe the cells on cover 24. Window 50 may be composed of Plexiglas and is preferably permanently bonded in place to the second support surface 32.

The support surface 34 of the water bath body 26 should be as thin as possible in order to speed heat transfer and maintain a small thermal gradient, but thick enough to accommodate ports 40 for the syringe needles 54 for fluids to enter and leave.

Cover 24 is held in place by the support surface 14 of the cell chamber body 12 and the pressure developed by the insertion of the second diameter portion 30 of the water bath body 26 into the interior of the cell chamber body 12. As noted above, the cell chamber body 12 and the water bath body 26 are joined by sidewall pressure due to close machining thereby eliminating the need for fasteners or the like.

An additional port (not shown) may be provided in the second diameter portion 30 of the water bath body 26 and associated with one of the passages 21 of the cell chamber body 12 in order to temporarily place a thermocouple wire for temperature calibration or for simultaneous measurement of fluid properties measurable by electrodes, e.g., pH, electrolytes. After calibration, the port is sealed, preferably with silicone cement.

Operation

Preliminary Procedures: All operations should be carried out with sterile technique and, ideally, in a laminar flow hood.

1. Presterilized 25 mm diameter covers 24 are placed into sterile petri plates side by side. If found to be necessary, 1 mL of a cell adhesive (e.g., Cell-Tak) is placed on the surface of the covers 24, the petri plate closed, incubated for one hour and then rinsed with a sterile buffer.

2. A suspension of approximately a small volume of cells of the desired cell line, at the appropriate numbers, and in the appropriate medium are placed onto the surface of the covers 24, the petri plate closed and then incubated overnight at the appropriate temperature, usually 37–42° C.

3. As a result of this treatment, the covers 24 become coated with adhered cells. The cover is gently rinsed with an appropriate medium (e.g., RPMI 1640) and then the cells are loaded with the desired fluorescence dye, typically by placing 1 mL of a 1–10 $\mu$M solution of the dye onto the covers 24 for one hour. A cover 24 is finally gently rinsed two-three times with benign basal medium and is ready now to be used in the temperature controlled cell perifusion chamber 48.

Water Bath Connections

1. Water from a thermoregulated water supplier is connecter to an inlet port 38 of the water bath chamber 52, and ideally is fed by gravity through the water bath chamber 52 or, by means of a peristaltic pump.

2. The water temperature and flow rate must have been previously adjusted so that it flows through the chamber 52 without causing excess vibration. The appropriate temperature of the circulating water is easily determined by temporarily placing a thermocouple on the outer (lower) surface of cover 24 of the assembled cell chamber structure 10 and adjusting the temperature of the circulating water appropriately. This temperature can be more accurately determined by inserting a thin wire thermocouple through a third port of the cell chamber body 12 of the assembled structure 10 and measuring inside the cell chamber 48.

Cell Chamber Connections:

1. A cover 24 onto which cells have adhered is gently placed onto the gasket 22 on the support surface 14 of the cell chamber body, with the side containing the cells facing up.

2. The cell chamber body 12 is then gently fitted onto the second diameter portion 30 of the water bath body and snapped into place in a slight interference fit arrangement, with an audible "click" which hermetically seals the cells inside the cell chamber. It is noted that this fit is such that the water bath body 26 can be separated by hand from the cell chamber body 12.

3. A tubing through which temperature regulated fluid will enter (e.g., 0.032" i.d.) is connected to a port 38 of the water bath body 26 and a second piece of tubing is connected to the other port 38 in the water bath body as a return line.

4. A tubing through which perifusion fluid will enter (e.g., 0.025" i.d.) is connected to a port 40 of the cell chamber body 12 and a second piece of tubing is connected to the other port 40 as a waste line.

5. While viewing the cells through the microscope under low power, appropriate bathing medium is infused into the cell perifusion chamber 48 sufficiently slowly that the cells do not detach.

6. At this point the cells can be observed continuously or semi-continuously with an inverted microscope or scanned with the laser and fluorescence measurements taken. The medium surrounding the cells in the cell chamber 48 can be changed at will.

The cell chamber structure 10 of the invention provides the following advantages:

1. Construction of the structure is of biocompatible plastic.

2. The structure is easily assembled and disassembled for cleaning and sterilizing, since the two parts of the chamber are held together by a high tolerance pressure fitting ("snap fitting").

3. Plastic construction minimizes weight.

4. Plastic construction permits inexpensive mass production by injection molding.

5. The ambient temperature of the cells can be rapidly changed because of the use of thermoregulated circulating water as a heat exchanger.

6. The dimensions can easily be changed to be accommodated into other holders. However, if the standard size of the cover 24 is altered then there may be a need for custom made covers 24.

7. The structure can be completely sealed to safely observe pathogens and other hazardous materials for prolonged periods of time, and 8. The optical path through the cell is uniform and not distorted significantly by assembly.

While designed specifically for the study of living cells, the structure 10 may also be used as a reaction chamber for the production of molecular products that absorb or scatter light and whose synthesis depends upon the repetitive heating and cooling of a reaction mixture, e.g., polymerase chain reactions The structure 10 is designed for operation at temperatures in the range of 0 to 90° C. and at normal atmospheric pressure. It is not designed for the much higher temperatures and pressures appropriate for studies in mineralogy, geology, crystallography and solid state physics.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A cell perifusion chamber structure comprising:
   a cell chamber body having a support surface with an aperture defined through said support surface, and wall structure extending upwardly from said support surface to define an interior, said wall structure including passages therein,
   a gasket disposed on said support surface so as not to cover said aperture,
   a first transparent cover disposed on said gasket and having a continuous surface so as to completely cover said aperture,
   a water bath body having a first portion and a second portion extending from said first portion, said first portion defining a second support surface, said second portion being received in said interior of said cell chamber body and being in interference fit arrangement with said wall structure, said water bath body having an interior support surface with an aperture therethrough, said aperture extending through said first and second portions, said first portion having first ports therein which communicate with said aperture of said water bath body, said second portion including second ports therein which communicate with said aperture of said water bath body and with associated said passages in said cell chamber body,
   a second transparent cover disposed on said interior support surface of said water bath body so as to divide said aperture of said water bath body into first and second portions, said second transparent cover having a continuous surface completely covering said second portion of said aperture to define a sealed cell chamber enclosed by said second transparent cover, said first transparent cover and surfaces of said cell chamber body,
   a transparent window disposed on said second support surface to cover said first portion of said aperture to define a water bath chamber enclosed by said transparent window, said second cover and surfaces of said water bath body, whereby the chamber is constructed and arranged to permit fluid to enter and exit said water bath chamber via said first ports to regulate temperature in said cell chamber via heat exchange therewith, and to permit perifusion fluid to enter and exit said cell chamber via said second ports.

2. The structure according to claim 1, wherein said cell chamber body and said water bath body are composed of biocompatible plastic.

3. The structure according to claim 1, wherein said first transparent cover is optically transparent.

4. The structure according to claim 3, wherein said first transparent cover is a glass microscope coverslip.

5. The structure according to claim 1, wherein said transparent window is bonded to said second support surface.

6. The structure according to claim 1, wherein said gasket is composed of elastomeric material.

7. The structure according to claim 6, wherein said material is one that can withstand being autoclaved or exposed to one normal hydrochloric acid or normal NaOH.

8. The structure according to claim 1, wherein said gasket is bonded to said support surface of said cell chamber body.

9. The structure according to claim 1, further comprising a hypodermic needles associated with each of said first and second ports for fluid entry and exit.

10. A cell perifusion chamber structure comprising:
    a cell chamber body having a support surface with an aperture defined through said support surface, and wall structure extending upwardly from said support surface to define an interior, said wall structure including passages therein,
    a gasket disposed on said support surface so as not to cover said aperture,
    a first transparent cover disposed on said gasket so as to cover said aperture,
    a water bath body having a first portion and a second portion extending from said first portion, said first portion defining a second support surface, said second portion being received in said interior of said cell chamber body and being in interference fit arrangement with said wall structure, said water bath body having an interior support surface with an aperture therethrough, said aperture extending through said first and second portions, said first portion having first ports therein which communicate with said aperture of said water bath body, said second portion including second ports therein which communicate with said aperture of said water bath body and with associated said passages in said cell chamber body,
    a second transparent cover disposed on said interior support surface of said water bath body so as to divide said aperture of said water bath body into first and second portions, said second transparent cover covering said second portion of said aperture to define a sealed cell chamber enclosed by said second transparent cover, said first transparent cover and surfaces of said cell chamber body,
    a transparent window disposed on said second support surface to cover said first portion of said aperture to define a water bath chamber enclosed by said transparent window, said second cover and surfaces of said water bath body, whereby the chamber is constructed and arranged to permit fluid to enter and exit said water bath chamber via said first ports to regulate temperature in said cell chamber via heat exchange therewith, and to permit perifusion fluid to enter and exit said cell chamber via said second ports,
    wherein said first and second portions of said water bath body are each cylindrical and said second portion has a diameter less than said first portion, said wall structure defining a cylindrical interior for receiving said second portion.

* * * * *